(12) United States Patent
Park

(10) Patent No.: US 11,511,049 B2
(45) Date of Patent: Nov. 29, 2022

(54) DRUG INJECTION DEVICE

(71) Applicant: MEGAGEN IMPLANT CO., LTD., Gyeongsan-si (KR)

(72) Inventor: Kwang Bum Park, Daegu (KR)

(73) Assignee: MEGAGEN IMPLANT CO., LTD.

( * ) Notice: Subject to any disclaimer, the term of this patent is extended or adjusted under 35 U.S.C. 154(b) by 339 days.

(21) Appl. No.: 15/035,220

(22) PCT Filed: Nov. 4, 2014

(86) PCT No.: PCT/KR2014/010509
§ 371 (c)(1),
(2) Date: May 6, 2016

(87) PCT Pub. No.: WO2015/069003
PCT Pub. Date: May 14, 2015

(65) Prior Publication Data
US 2016/0263332 A1 Sep. 15, 2016

(30) Foreign Application Priority Data

Nov. 7, 2013 (KR) .......................... 10-2013-0135078

(51) Int. Cl.
*A61M 19/00* (2006.01)
*A61M 5/20* (2006.01)
(Continued)

(52) U.S. Cl.
CPC .... *A61M 5/31581* (2013.01); *A61M 5/14546* (2013.01); *A61M 5/20* (2013.01);
(Continued)

(58) Field of Classification Search
CPC ............ A61M 5/3158; A61M 5/31581; A61M 5/14546; A61M 5/31513; A61M 5/482; A61M 5/14566
See application file for complete search history.

(56) References Cited

U.S. PATENT DOCUMENTS

| 4,747,824 A * | 5/1988 | Spinello | .................. A61M 5/20 604/512 |
| 4,942,352 A * | 7/1990 | Sano | ....................... H02J 50/70 320/164 |

(Continued)

FOREIGN PATENT DOCUMENTS

| CN | 1276735 A | 12/2000 |
| CN | 102014987 A | 4/2011 |

(Continued)

*Primary Examiner* — Bhisma Mehta
*Assistant Examiner* — William R Frehe
(74) *Attorney, Agent, or Firm* — Renaissance IP Law Group LLP

(57) ABSTRACT

A drug injection device is disclosed. A drug injection device, according to the present invention, comprises: an injection unit which is provided with an ampoule accommodation portion for accommodating an ampoule that contains an injectable solution, and injects the injectable solution into a person being operated on; and an injection speed adjustment unit which is connected to the injection unit, applies pressure to the injectable solution, and adjusts the injection speed of the injectable solution, being injected into the body of the person being operated on, by selectively adjusting the speed of the pressure applied to the injectable solution, wherein the injection speed adjustment unit comprises: an injection unit attachment portion to which the ampoule accommodation portion is detachably attached; a pressurizing plunger which is connected to the ampoule accommodated in the ampoule accommodation portion and applies pressure to the injectable solution; and a pressurizing plunger up/down driving module which is provided on the same axis as the pressurizing plunger and drives the pressurizing plunger up or down.

11 Claims, 13 Drawing Sheets

(51) Int. Cl.
  *A61M 5/315* (2006.01)
  *A61M 5/145* (2006.01)
  *A61M 5/24* (2006.01)
  *A61M 5/31* (2006.01)
  *A61M 5/48* (2006.01)

(52) U.S. Cl.
  CPC ............ *A61M 5/24* (2013.01); *A61M 5/3158* (2013.01); *A61M 19/00* (2013.01); *A61M 5/2466* (2013.01); *A61M 5/3148* (2013.01); *A61M 5/31513* (2013.01); *A61M 5/31515* (2013.01); *A61M 5/482* (2013.01); *A61M 2005/247* (2013.01); *A61M 2005/31521* (2013.01); *A61M 2205/8243* (2013.01); *A61M 2210/0625* (2013.01)

(56) References Cited

U.S. PATENT DOCUMENTS

| | | | | |
|---|---|---|---|---|
| 5,180,371 | A * | 1/1993 | Spinello | A61M 5/2053 604/512 |
| 5,720,728 | A * | 2/1998 | Ford | A61M 3/0233 604/141 |
| 6,022,337 | A * | 2/2000 | Herbst | A61M 5/14566 604/131 |
| 8,002,736 | B2 * | 8/2011 | Patrick | A61B 8/0841 604/82 |
| 2006/0102174 | A1 | 5/2006 | Hochman | |
| 2009/0308386 | A1 * | 12/2009 | Kronestedt | A61M 5/20 604/311 |
| 2010/0331678 | A1 * | 12/2010 | Fago | A61M 5/14546 600/432 |
| 2012/0035472 | A1 * | 2/2012 | Bruce | A61M 5/14546 600/432 |
| 2013/0041258 | A1 | 2/2013 | Patrick et al. | |
| 2013/0126559 | A1 * | 5/2013 | Cowan | A61M 5/31525 222/386 |
| 2013/0281965 | A1 * | 10/2013 | Kamen | A61M 5/142 604/67 |
| 2013/0310756 | A1 * | 11/2013 | Whalley | A61M 5/31 604/189 |

FOREIGN PATENT DOCUMENTS

| | | |
|---|---|---|
| CN | 102387826 A | 3/2012 |
| CN | 103037921 A | 4/2013 |
| EP | 0980687 A1 | 2/2000 |
| EP | 2066276 A2 | 6/2009 |
| JP | 2001514053 A | 9/2001 |
| JP | 2002045421 | 2/2002 |
| JP | 2010535039 A | 11/2010 |
| KR | 20010023682 | 3/2001 |
| KR | 101092074 | 12/2011 |
| KR | 101121082 | 3/2012 |
| KR | 101261408 | 5/2013 |

* cited by examiner

FIG. 8
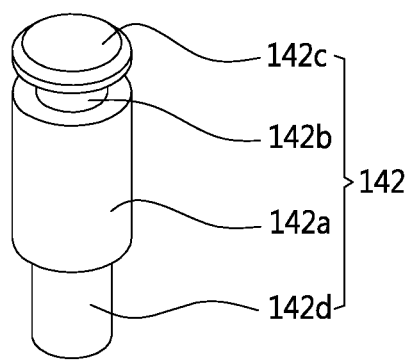
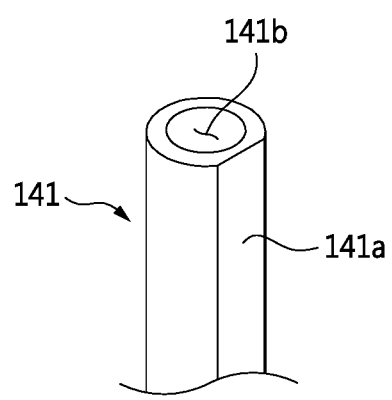

DRUG INJECTION DEVICE

TECHNICAL FIELD

The present invention relates to a drug injection device, and more particularly, to a drug injection device capable of injecting an injectable solution into the body of a person being operated on without causing pain to the person being operated on by adjusting an injection speed of the injectable solution which is injected into the body of the person being operated on.

BACKGROUND ART

An implant means a substitute that restores original human tissue when the original human tissue is lost, but indicates a series of operations that implants an artificially made tooth in the dentist.

When the implant is described in brief, the implant is an operation that implants a fixture which is a root of the tooth made of titanium without a rejection response to a human body, and the like in an alveolar bone which the tooth leaves so as to substitute for the lost tooth root and thereafter, fixes the artificial tooth to restore a function of the tooth.

The implant operation is diversified according to a type of the fixture, but is generally completed by punching an insertion location by using a predetermined drill and thereafter, inserts the fixture in the tooth bone and osseointegrates the fixture to a bone and couples an abutment to the fixture and thereafter, covers the abutment with a final prosthesis.

Neighbor teeth and bones of a general prosthesis or denture are emaciated, but the implant does not emaciate an adjacent dental tissue and has the same function or shape as a natural tooth and does not cause a decayed tooth, and as a result, the implant can be semipermanently used.

Further, the implant operation recovers a single lost tooth and promotes a function of the denture for patients having no partial tooth and complete tooth, enhances an aesthetic aspect of recovery of tooth prosthesis, distributes excessive stress applied to a neighbor supporting bone tissue and assists stabilization of a set of teeth.

Meanwhile, the implant operation performs gum incision, the punching by the drill, and the like during the operation to cause a lot of pains to a person being operated on. Therefore, in the implant operation, local anesthesia of an operation portion is required.

The local anesthesia is generally performed by pressing an anesthesia solution with a syringe to inject the anesthesia solution in the operation portion. In this case, when an injection speed of the anesthesia solution, that is, a pressing speed of the anesthesia solution is high, excessive pressure is generated at an injection portion of the anesthesia solution, and as a result, the person being operated on feels a pain.

Accordingly, the anesthesia solution needs to be injected slowly as possible. However, when the injection speed of the anesthesia solution decreases, an injection time of the anesthesia solution increases, consequently, a time for which the operator holds the syringe increases.

When the time for which the operator holds the syringe increases, it is difficult for the operator to maintain a constant injection speed and the person being operated on feels the pain due to a hand vibration phenomenon. Accordingly, in order to solve the problem, a drug injection device of a scheme in which the person being operated on presses the anesthesia solution through a separate pressing mechanism without directly pressing the anesthesia solution is required.

Further, miniaturization or slimming of the drug injection device is required and development of a drug injection device in which a layout of internal components is optimized is required for achieving the miniaturization or slimming.

DISCLOSURE

Technical Problem

The present invention is directed to provide a drug injection device in which it is not necessary for a person being operated on to directly pressurize an injectable solution for injection of the injectable solution such as an anesthesia solution and a layout of the internal components is optimized to reduce the drug injection device in size and thickness.

Technical Solution

One aspect of the present invention provides a drug injection device, comprising: an injection unit which is provided with an ampoule accommodation portion for accommodating an ampoule that contains an injectable solution, and injects the injectable solution into a person being operated on; and an injection speed adjustment unit which is connected to the injection unit, applies pressure to the injectable solution, and adjusts the injection speed of the injectable solution, being injected into the body of the person being operated on, by selectively adjusting the speed of the pressure applied to the injectable solution, in which the injection speed adjustment unit comprises: an injection unit attachment portion to which the ampoule accommodation portion is detachably attached; a pressurizing plunger which is connected to the ampoule accommodated in the ampoule accommodation portion and applies pressure to the injectable solution; and a pressurizing plunger up/down driving module which is provided on the same axis as the pressurizing plunger and drives the pressurizing plunger up or down.

The pressurizing plunger up/down driving module may comprise a lead screw engaging with the pressurizing plunger; a driving motor which rotates the lead screw; and a guide portion that guides movement of the pressurizing plunger.

The guide portion may comprise a rotation stop portion which stops the rotation of the pressurizing plunger.

The rotation stop portion may comprise a non-curved inner wall portion which is shape-matched with a non-curved side portion formed on an outer wall of the pressurizing plunger.

The pressurizing plunger may comprise a plunger main body having a female thread engaging with the lead screw provided on the inner wall portion; and a plunger cap which is attached to the upper end of the plunger main body.

The plunger cap may comprise a cap body portion connected to the plunger main body and having a cylindrical shape; a neck portion connected to the cap body portion and having a cross-section area smaller than that of the cap body portion; and a cap head portion connected to the neck portion and having a cross-section area larger than that of the neck portion.

The plunger cap may further comprise an airtight member supported by the neck portion.

The injection unit attachment portion may comprise a body portion for injection unit attachment provided in an insertion groove to which the end region of the ampoule accommodation portion is inserted; and a locking jaw portion provided at the body portion for injection unit attachment and locked to a projection member projecting in a lateral direction from the outer wall of the ampoule accommodation portion when the ampoule accommodation portion rotates.

The locking jaw portion may comprise an upper locking jaw supporting the upper end of the projection member; and a lower locking jaw supporting the lower end of the projection member and elastically biased toward the upper locking jaw.

The locking jaw portion may further comprise a stopper which supports the front end of the projection member and limits the rotation of the ampoule accommodation portion of the projection member.

The injection speed adjustment unit may further comprise a waterproof portion through which the pressurizing plunger passes and that prevents a liquid from penetrating to the inside of the injection speed adjustment unit.

The waterproof portion may comprise a waterproof portion body with a through-hole through which the pressurizing plunger passes; and a watertight member supported by the waterproof portion body and sealing a gap between the outer wall of the pressurizing plunger and the side wall of the through-hole.

The injection speed adjustment unit may further comprise a control unit that controls the pressurizing plunger up/down driving module to vary the pressurizing speed of the pressurizing plunger; and a controller portion electrically connected with the control unit.

The injection unit may comprise a tube connected to the ampoule accommodation portion; a needle holder connected to the tube; and an intra-injection needle attached to the needle holder.

The ampoule accommodation portion may comprise an accommodation portion main body accommodated with the ampoule; and an ampoule needle attached to the accommodation portion main body and communicating with the tube.

The drug injection device may further comprise a switch unit which is attached to the injection unit and connected to the control unit wiredly or wirelessly to transmit a signal to the control unit.

The switch unit may comprise: a panel portion with a button which turns on/off the pressurization of the injectable solution; and a panel bracket which is attached to the injection unit and supports the panel portion.

The drug injection device may further comprise a chargeable battery which is provided in the injection speed adjustment unit and supplies power to the driving motor; a first coil which is provided in the injection speed adjustment unit and charges the chargeable battery; and a non-contact charging cradle which are non-contacted to the first coil and provided with a second coil supplying electric energy to the first coil.

The injection speed adjustment unit may further comprise a needle holder bracket gripping the needle holder.

Advantageous Effects

According to the exemplary embodiments of the present invention, it is not necessary for a person being operated on to directly pressurize an injectable solution for injection of the injectable solution by pressurizing the injectable solution by the pressurizing plunger of the injection speed adjustment unit, and the pressurizing plunger up/down driving module which drives the pressurizing plunger up or down is provided on the same axis as the pressurizing plunger to reduce the injection speed adjustment unit in size and thickness.

DESCRIPTION OF DRAWINGS

FIG. 8 is a diagram illustrating a plunger cap and a plunger main body of FIG. 7.

MODES OF THE INVENTION

In order to sufficiently understand an operating advantage of the present invention and an object achieved by the present invention and exemplary embodiments of the present invention, the accompanying drawings illustrating the exemplary embodiments of the present invention and contents disclosed in the accompanying drawings should be referred.

Hereinafter, the exemplary embodiments of the present invention are described with reference to the accompanying drawings to describe the present invention in detail. However, in describing the present invention, a detailed description of already known functions or configurations will be omitted so as to make the subject matter of the present invention clear.

Figure 1:
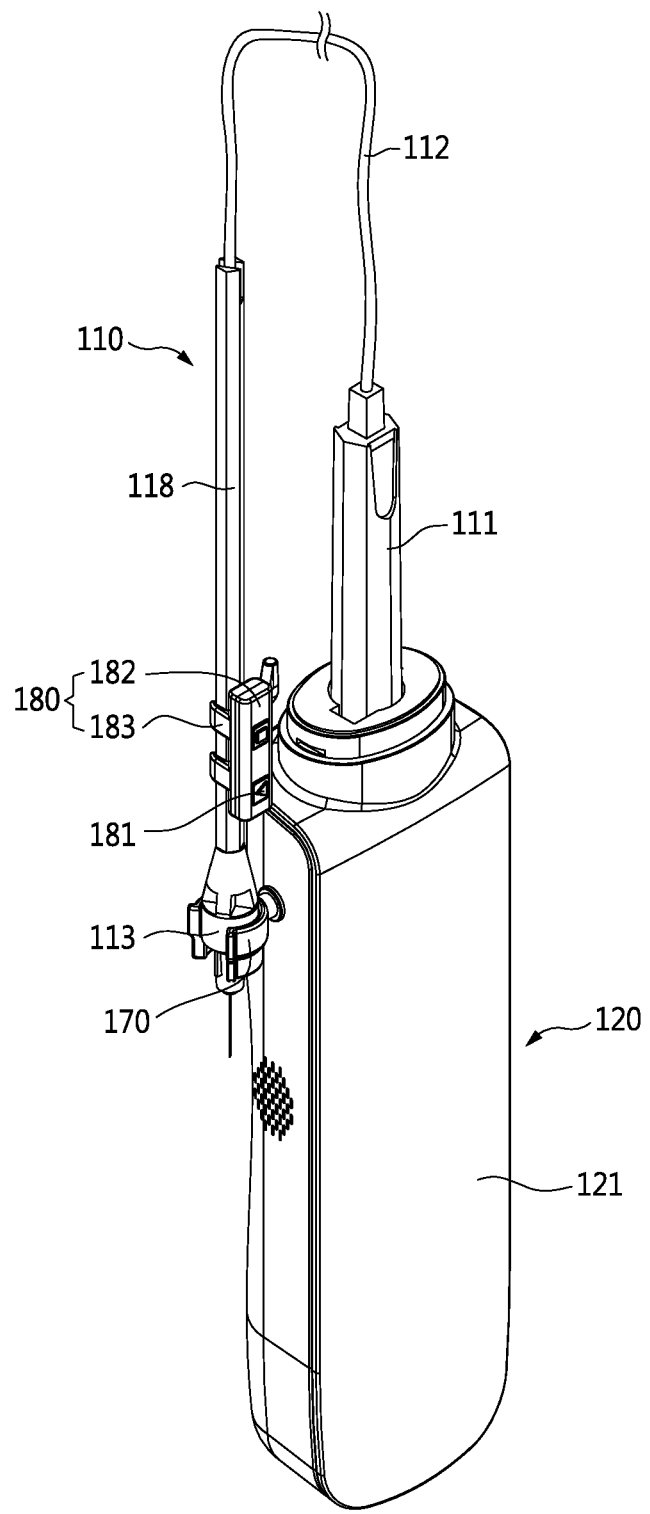
FIG. 1 is a perspective view illustrating a drug injection device according to an exemplary embodiment of the present invention.
Figure 2:
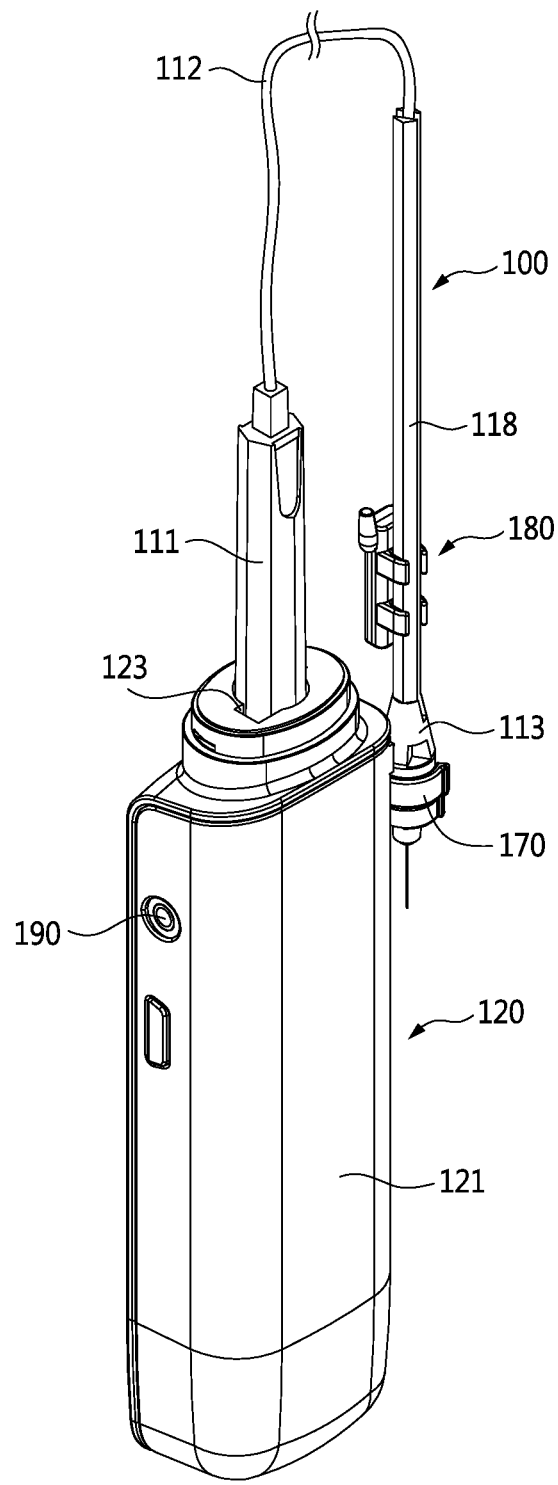
FIG. 2 is a perspective view of FIG. 1 viewed in another direction.
Figure 3:
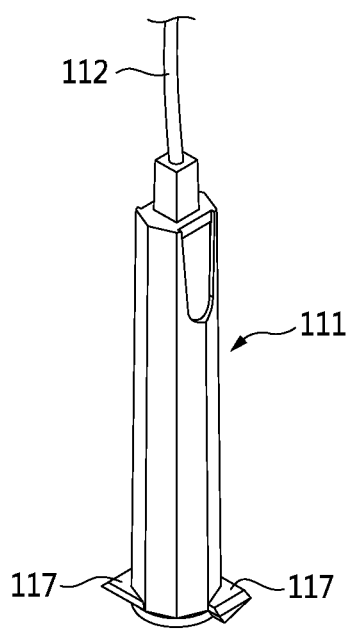
FIG. 3 is a perspective view illustrating an ampoule accommodation portion of FIG. 1.
Figure 4:
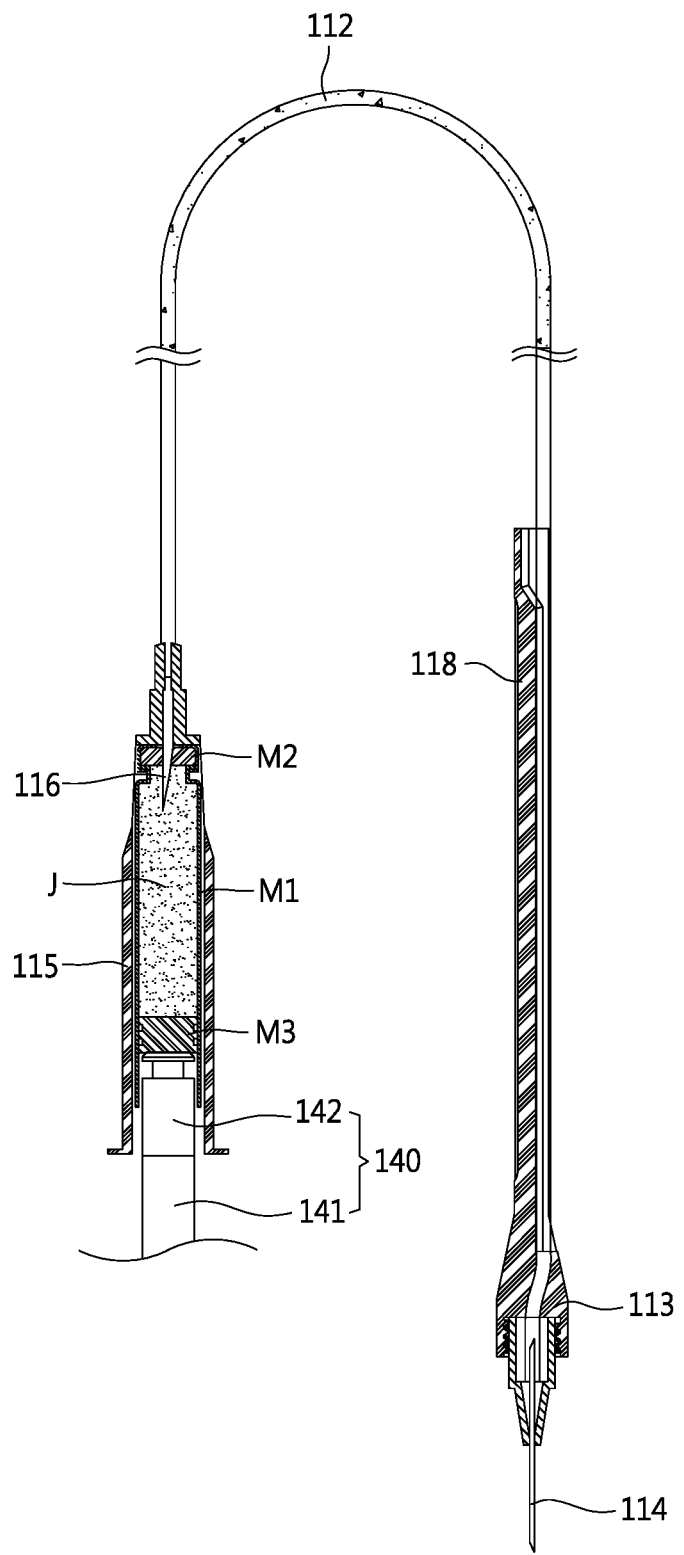
FIG. 4 is a diagram illustrating the inside of an injection unit of FIG. 1.
Figure 5:
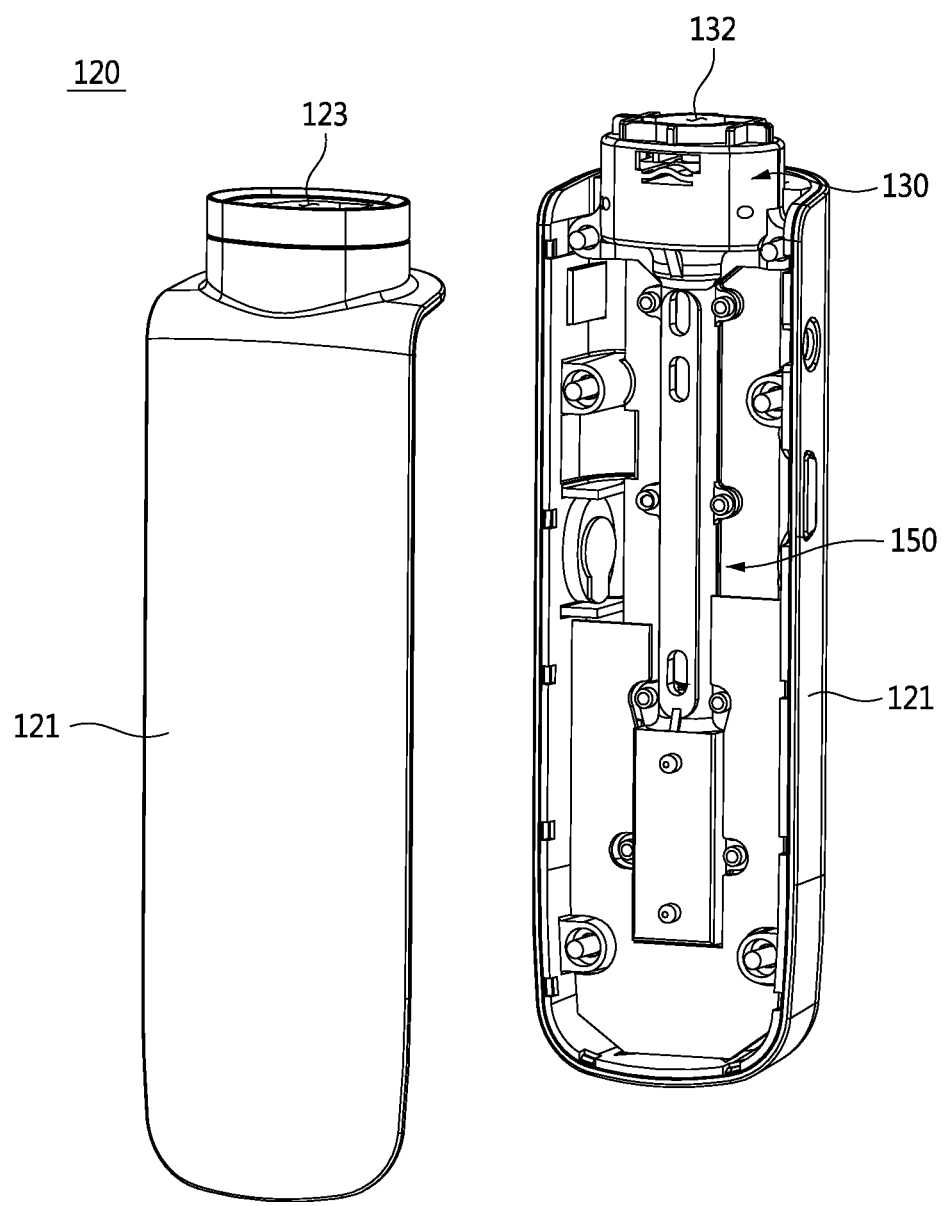
FIG. 5 is a diagram illustrating an injection speed adjustment unit of FIG. 1.
Figure 6:
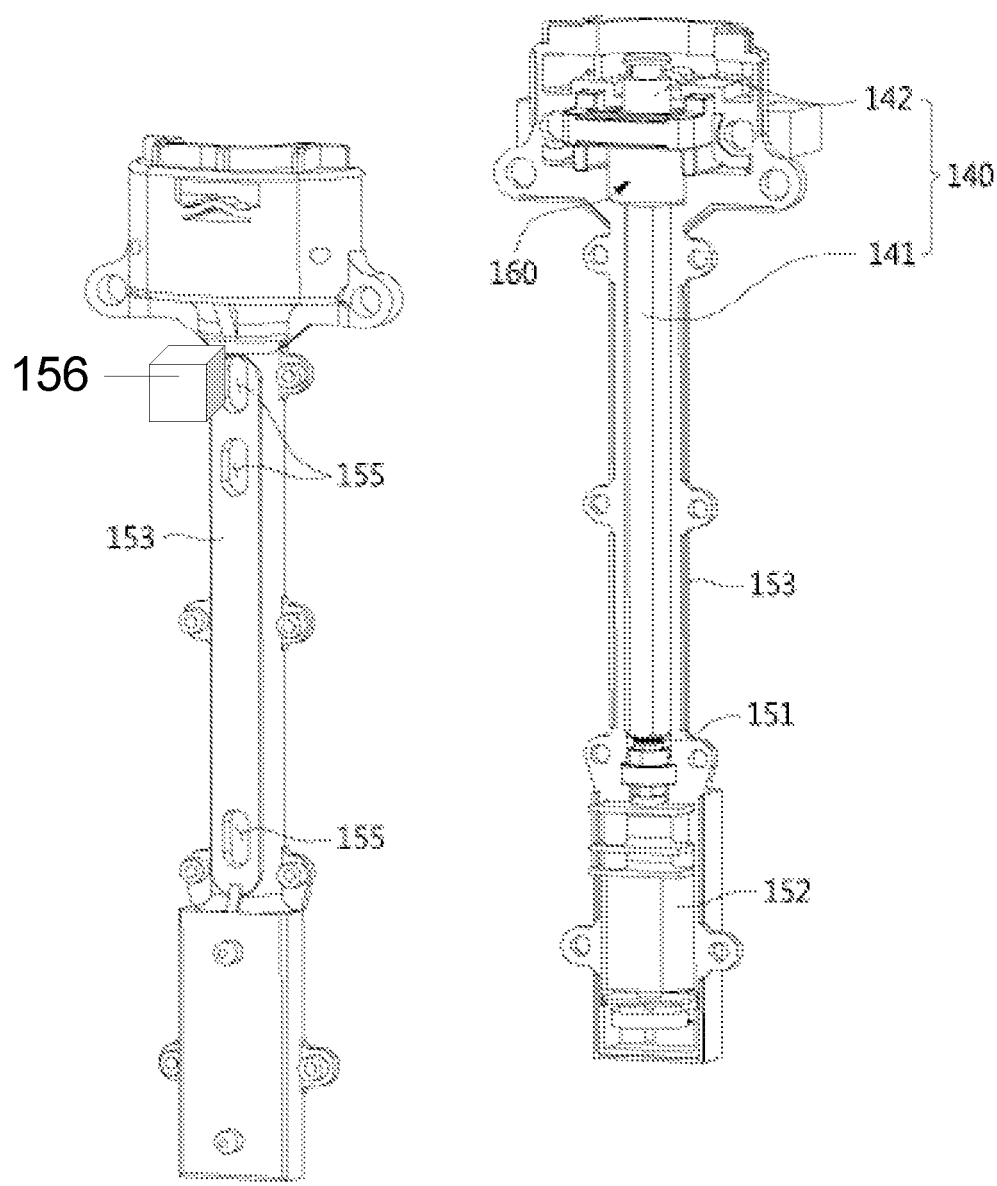
FIG. 6 is a diagram illustrating a pressurizing plunger up/down driving module of FIG. 5.
Figure 7:
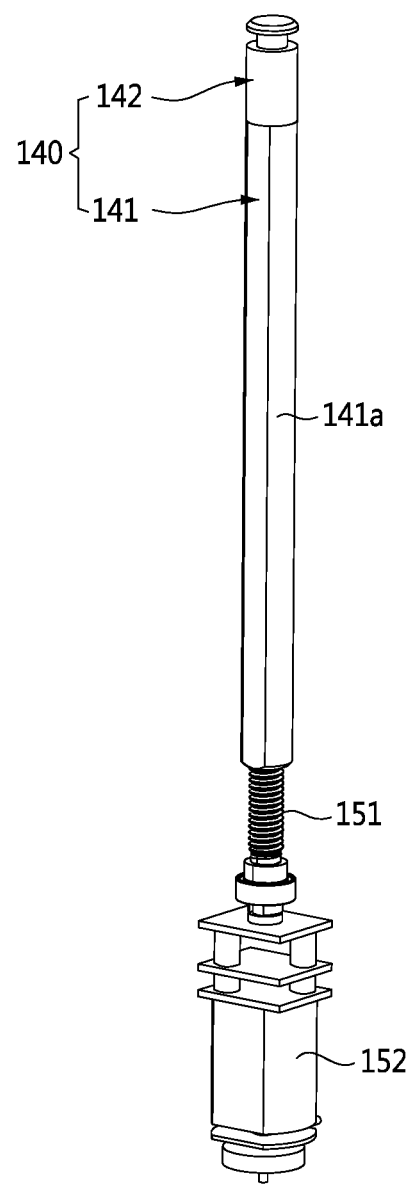
FIG. 7 is a diagram illustrating a lead screw of FIG. 6.
Figure 9:
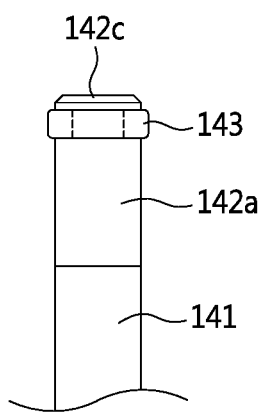
FIG. 9 is a diagram illustrating that an airtight member is attached to the plunger cap of FIG. 7.
Figure 10:
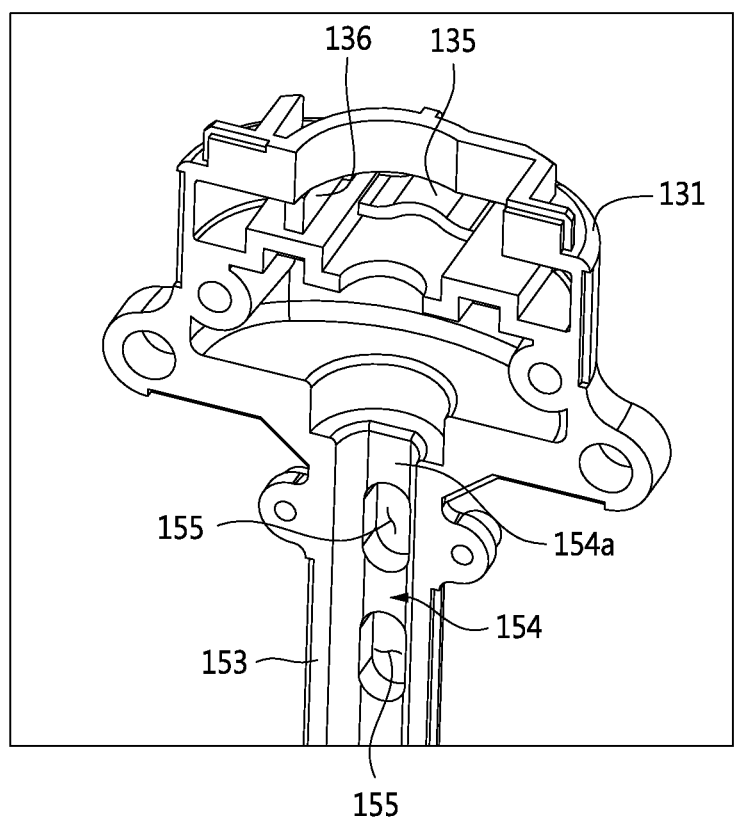
FIG. 10 is a diagram illustrating a guide portion of FIG. 6.
Figure 11:
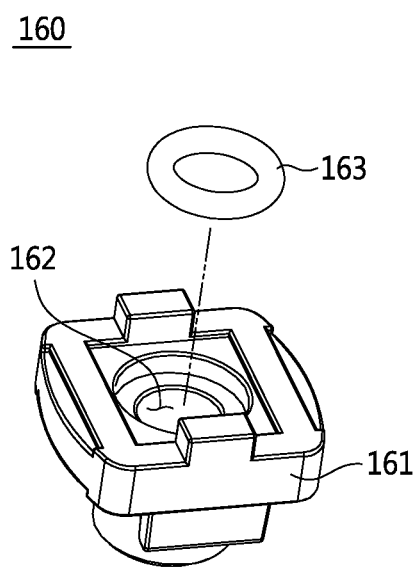
FIG. 11 is a diagram illustrating a waterproof portion of FIG. 6.
Figure 12:
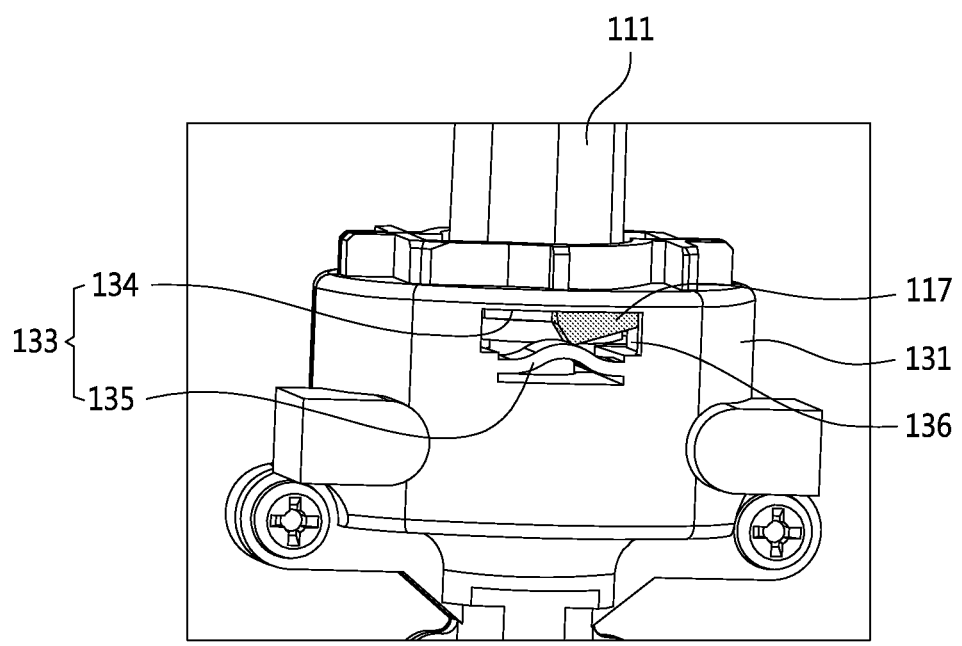
FIG. 12 is a diagram illustrating an injection unit attachment portion of FIG. 5.
Figure 13:
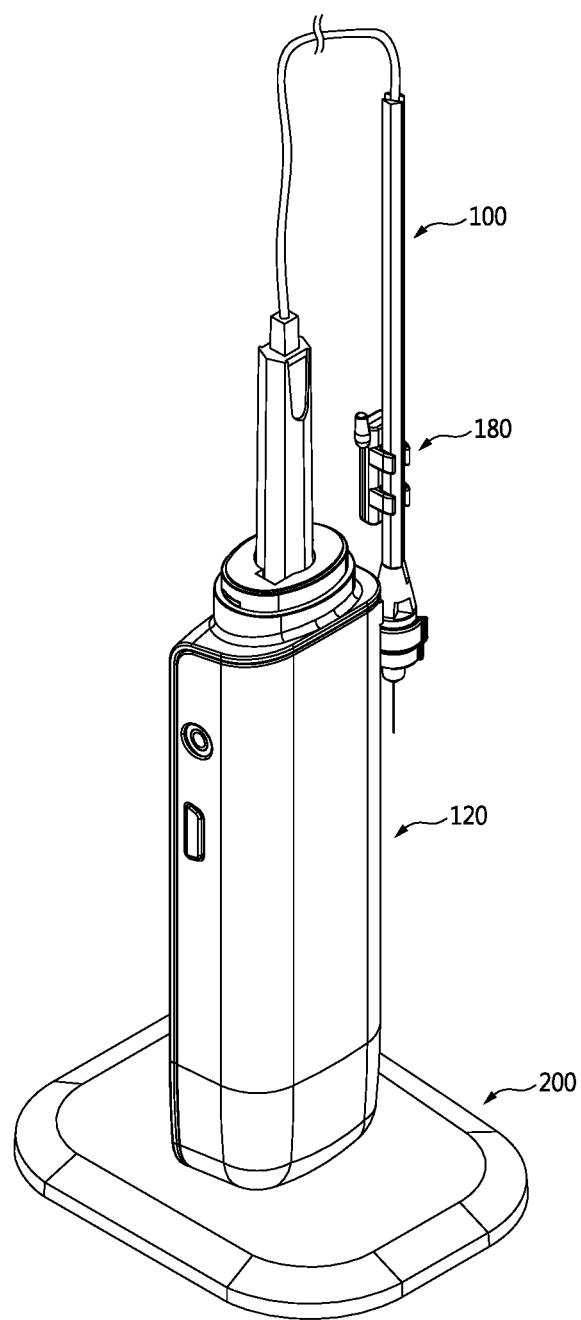
FIG. 13 is a diagram illustrating that the injection speed adjustment unit of FIG. 1 is held on a non-contact charging cradle.

FIG. 1 is a perspective view illustrating a drug injection device according to an exemplary embodiment of the present invention, FIG. 2 is a perspective view of FIG. 1 viewed in another direction, FIG. 3 is a perspective view illustrating an ampoule accommodation portion of FIG. 1, FIG. 4 is a diagram illustrating the inside of an injection unit of FIG. 1, FIG. 5 is a diagram illustrating an injection speed adjustment unit of FIG. 1, FIG. 6 is a diagram illustrating a pressurizing plunger up/down driving module of FIG. 5, FIG. 7 is a diagram illustrating a lead screw of FIG. 6, FIG. 8 is a diagram illustrating a plunger cap and a plunger main body of FIG. 7, FIG. 9 is a diagram illustrating that an airtight member is attached to the plunger cap of FIG. 7, FIG. 10 is a diagram illustrating a guide portion of FIG. 6, FIG. 11 is a diagram illustrating a waterproof portion of FIG. 6, FIG. 12 is a diagram illustrating an injection unit attachment portion of FIG. 5, and FIG. 13 is a diagram illustrating that the injection speed adjustment unit of FIG. 1 is held on a non-contact charging cradle.

As illustrated in FIGS. 1 to 13, a drug injection device according to an exemplary embodiment of the present invention includes an injection unit 110 which is provided with an ampoule accommodation portion 111 for accommodating an ampoule M that contains an injectable solution J, and injects the injectable solution J into a person being operated on, and an injection speed adjustment unit 120 which is connected to the injection unit 110, applies pressure to the injectable solution J, and adjusts the injection speed of the injectable solution J, being injected into the body of the person being operated on, by selectively adjusting the speed of the pressure applied to the injectable solution.

The injection speed adjustment unit 120 includes an injection unit attachment portion 130 to which the ampoule accommodation portion 111 is detachably attached, a pressurizing plunger 140 which is connected to the ampoule M accommodated in the ampoule accommodation portion 111 and applies pressure to the injectable solution J, and a pressurizing plunger up/down driving module 150 which is provided on the same axis as the pressurizing plunger 140 and drives the pressurizing plunger up or down.

The injectable solution J of the exemplary embodiment means various drugs such as an anesthesia solution which are injected into the body of the person being operated on.

Further, in the exemplary embodiment, the ampoule M accommodates the injectable solution J. The ampoule M includes an ampoule body M1 having a pipe shape with two opened ends, a sealing cap M2 sealing one opening of the ampoule body M1, and a piston M3 sealing the other opening of the ampoule body M1 and movable along the inner wall of the ampoule body M1.

The piston M3 is connected to the pressurizing plunger 140 of the injection speed adjustment unit 120 to pressurize the injectable solution J accommodated in the ampoule M by an operation of the injection speed adjustment unit 120.

Meanwhile, the injection unit 110 injects the injectable solution J to the person being operated on. The injection unit 110 includes an ampoule accommodation portion 111 which is detachably attached to the injection unit attachment portion 130 of the injection speed adjustment unit 120 and accommodates the ampoule M, a tube connected to the ampoule accommodation portion 111, a needle holder 113 connected to the tube 112, and an intra-injection needle 114 attached to the needle holder 113.

The ampoule accommodation portion 111 accommodates the ampoule M and is detachably attached to the injection unit attachment portion 130 of the injection speed adjustment unit 120. The ampoule accommodation portion 111 includes an accommodation portion main body 115 accommodated with the ampoule M, and an ampoule needle 116 which is attached to the accommodation portion main body 115 and communicates with the tube 112.

In the accommodation portion main body 115, as illustrated in FIG. 4, the inside is hollow and the end portion is opened so that the ampoule M enters the inside of the accommodation portion main body 115. Further, the accommodation portion main body 115 includes a projection member 117 which is projected in a lateral direction from the outer wall of the end region of the accommodation portion main body 115.

In the exemplary embodiment, the projection members 117 make a pair and are symmetrical based on a central axis of the accommodation portion main body 115.

The accommodation portion main body 115 is locked to the injection unit attachment portion 130 of the injection speed adjustment unit 120 by the projection member 117, and for convenience of description, a structure of the injection unit attachment portion 130 will be described below.

The ampoule needle 116 is attached to the upper wall of the accommodation portion main body 115 and communicates with the tube 112. The ampoule needle 116 passes through the sealing cap M2 of the ampoule M to communicate with the inside of the ampoule M when the ampoule M is accommodated in the accommodation portion main body 115.

The tube 112 is connected to the ampoule accommodation portion 111 and communicates with the ampoule needle 116. Further, the needle holder 113 is connected to the tube 112 and communicates with the tube 112. Accordingly, the injectable solution J in the ampoule M flows to the needle holder 113 through the tube 112.

The intra-injection needle 114 is attached to the needle holder 113 and communicates with the needle holder 113. Accordingly, the injectable solution J flowing to the needle holder 113 is injected to the person being operated on through the intra-injection needle 114.

Further, the injection unit 110 further includes a rod-shaped handle portion 118 connected to the needle holder 113. The handle portion 118 provides convenience of the operation so that the person being operated on may simply grip the injection unit 110.

Meanwhile, the injection speed adjustment unit 120 is connected to the injection unit 110 to apply pressure to the injectable solution J and selectively adjusts a speed of the pressure applied to the injectable solution J to adjust the injection speed of the injectable solution J which is injected into the body of the person being operated on.

The injection speed adjustment unit 120 includes an injection unit attachment portion 130 to which the ampoule accommodation portion 111 is detachably attached, a pressurizing plunger 140 which is connected to the ampoule M accommodated in the ampoule accommodation portion 111 and applies pressure to the injectable solution J, and a pressurizing plunger up/down driving module 150 which is provided on the same axis as the pressurizing plunger 140 and drives the pressurizing plunger up or down.

Further, the injection speed adjustment unit 120 further includes a housing 121 which accommodates the injection unit attachment portion 130, the pressurizing plunger 140, and the pressurizing plunger up/down driving module 150. Further, a passing hole 123 for connection between the ampoule accommodation portion 111 and the injection unit attachment portion 130 is provided in the housing 121.

The pressurizing plunger 140 is moved by the pressurizing plunger up/down driving module 150 to apply the pressure to the piston M3 of the ampoule M. The pressurizing plunger 140 includes a plunger main body 141 connected to the pressurizing plunger up/down driving module 150 and a plunger cap 142 attached to the upper end of the plunger main body 141.

The plunger main body 141 is hollow to has a rob shape. On the inner wall portion of the plunger main body 141, a female thread (not illustrated) which engages with the lead screw to be described below is provided.

Further, on the outer wall of the plunger main body 141, a non-curved side portion 141a disposed in a lateral direction is provided. Accordingly, in the embodiment, the plunger main body 141 is provided in a cylindrical shape in which a part of the outer peripheral surface is cut in the lateral direction.

The plunger cap 142 is attached to the upper end of the plunger main body 141. The plunger cap 142 includes a cap body portion 142a connected to the plunger main body 141 and having a cylindrical shape, a neck portion 142b connected to the cap body portion 142a and having a cross-section area smaller than that of the cap body portion 142a, and a cap head portion 142c connected to the neck portion 142b and having a cross-section area larger than that of the neck portion 142b.

The cap body portion 142a is fitted to the upper end of the plunger main body 141. At the end portion of the cap body portion 142a, a fitting projection 142d which is fitted into a fitting groove 141b which is dented at the front end of the plunger main body 141 is projected.

Further, the plunger cap 142 further includes an airtight member 143 supported by the neck portion 142b. The airtight member 143 is provided with a ring-shaped flexible rubber seal. In the exemplary embodiment, an outer diameter of the airtight member 143 is larger than those of the cap head portion 142c and the cap body portion 142a.

The airtight member 143 is used at the time of an aspiration operation. Generally, the aspiration procedure means a procedure of pulling the plunger of an injector in order to verify whether an injection needle penetrates to a blood vessel (artery or vein) after the injection needle is stuck to the person being operated on.

When describing the aspiration operating method performed in the exemplary embodiment, the airtight member 143 is in closer contact with the inner wall of the ampoule body M1 and thus, external air does not flow into a space between the piston M3 and the airtight member 143. In this state, when the pressurizing plunger 140 descends, negative pressure is generated in the space between the piston M3 and the airtight member 143 and as a result, the piston M3 descends.

The airtight member 143 is used for the aspiration operation, and in the case where the aspiration operation is not performed, the airtight member 143 may be removed from the plunger cap 142.

Meanwhile, the pressurizing plunger up/down driving module 150 is provided on the same axis as the pressurizing plunger 140 and drives the pressurizing plunger 140 up or down.

The pressurizing plunger up/down driving module 150 includes a lead screw 131 engaging with the pressurizing plunger 140, a driving motor 152 which rotates the lead screw 151, and a guide portion 153 which guides movement of the pressurizing plunger 140.

The lead screw 131 engages with a female thread (not illustrated) of the plunger main body 141 and rotates by the driving motor 152 to drive the pressurizing plunger 140 up or down.

The guide portion 153 is connected to the pressurizing plunger 140 to guide the movement of the pressurizing plunger 140. The guide portion 153 includes a rotation stop portion 154 which stops the rotation of the pressurizing plunger 140.

In the exemplary embodiment, the rotation stop portion 154 includes a non-curved inner wall portion 154a shape-matched with a non-curved side portion 141a of an outer wall of the pressurizing plunger 140.

As such, the non-curved inner wall portion 154a of the guide portion 153 is shape-matched with the non-curved side portion 141a of the pressurizing plunger 140, and as a result, the pressurizing plunger 140 does not rotate along the lead screw 151 and slightly moves in a vertical direction when the lead screw 151 rotates.

Further, the guide portion 153 is provided with a plurality of exposure holes 155 which exposes the pressurizing plunger 140. The exposure hole 155 is to recognize the location of the pressurizing plunger 140, and a detection sensor, e.g., illustrated at 156, is provided at a position which is adjacent to the exposure hole 155 in the injection speed adjustment unit 120 according to the exemplary embodiment. The detection sensor, e.g., illustrated at 156, detects whether the pressurizing plunger 140 is exposed in each exposure hole 155 during up/down of the pressurizing plunger 140.

Meanwhile, the ampoule accommodation portion 111 is detachably attached to the injection unit attachment portion 130. The injection unit attachment portion 130 includes a body portion 131 for injection unit attachment provided in an insertion groove 132 to which the end region of the ampoule accommodation portion 111 is inserted, and a locking jaw portion 133 provided at the body portion 131 for injection unit attachment and locked to a projection member 117 of the ampoule accommodation portion 111 when the ampoule accommodation portion 111 rotates.

The insertion groove 132 provided in the body portion 131 for injection unit attachment communicates with the passing hole 123 of the housing 121.

The locking jaw portion 133 includes an upper locking jaw 134 supporting the upper end of the projection member 117 and a lower locking jaw 135 supporting the lower end of the projection member 117 and elastically biased toward the upper locking jaw 134.

In the exemplary embodiment, the lower locking jaw 135 has a plate shape and both side portions are fixed to the body portion 131 for injection unit attachment. Further, the lower locking jaw 135 is bent so that the height is increased toward the center from the both side portions to more efficiently apply the pressure to the projection member 117. Further, the lower locking jaw 135 may smoothly move the projection member 117 when the ampoule accommodation portion 111 rotates b the bent center.

Further, the locking jaw portion 133 further includes a stopper 136 that supports the front end of the projection member 117 and limits the rotation of the ampoule accommodation portion 111 of the projection member 117. The stopper 136 is in contact to the front end of the projection member 117 to stop the rotation of the ampoule accommodation portion 111 when the ampoule accommodation portion 111 rotates at a predetermined angle.

Meanwhile, the injection speed adjustment unit 120 includes a waterproof portion 160 through which the pressurizing plunger 140 passes and that prevents a liquid from penetrating to the inside of the injection speed adjustment unit 120.

The waterproof portion 160 includes a waterproof portion body 161 with a through-hole 162 through which the pressurizing plunger 140 passes and a watertight member 163 supported by the waterproof portion body 161 and sealing a gap between the outer wall of the pressurizing plunger and the side wall of the through-hole 162.

In the exemplary embodiment, the watertight member 163 is provided with an O-ring. The watertight member 163 is in close contact with the outer wall of the pressurizing plunger 140 and seals the gap between the outer wall of the pressurizing plunger 140 and the side wall of the through-hole 162 to prevent the liquid from penetrating into the injection speed adjustment unit 120 when the insertion groove 132 is cleaned.

Meanwhile, the injection speed adjustment unit 120 further includes a control unit (not illustrated) that controls the pressurizing plunger up/down driving module 150 to vary the pressurizing speed of the pressurizing plunger 140, and a controller portion (not illustrated) electrically connected with the control unit.

The control unit is provided at the inside of the injection speed adjustment unit 120 and the controller portion (not illustrated) is exposed to the outside of a case 121. The controller portion (not illustrated) inputs the pressurizing speed of the pressurizing plunger 140 which is selected by the operator to the control unit. Further, a button (not illustrated) which inputs the pressurizing and the pressurizing stop of the pressurizing plunger 140 is provided in the controller portion (not illustrated).

Meanwhile, the injection speed adjustment unit 120 further includes a needle holder bracket 170 gripping the needle holder 113. The needle holder bracket 170 is attached to the housing 121 and grips the needle holder 113 to be easily portable with the injection unit 110.

Further, in the injection speed adjustment unit 120, a connection jack 190 to which a switch unit 180 to be described below is wiredly connected is provided.

Meanwhile, the drug injection device further includes a switch unit 180 which is attached to the injection unit 110 and connected to the control unit wiredly or wirelessly to transmit a signal to the control unit.

The switch unit 180 includes a panel portion with a button 181 which turns on/off the pressurization of the injectable solution J and a panel bracket 183 which is attached to the injection unit 110 and supports a panel portion 182. In the exemplary embodiment, the panel bracket 183 is detachably attached to a handle portion 118 of the injection unit 110.

Through the switch unit 180, the operator may easily control the injection and the injection stop of the injectable solution J without using the controller portion (not illustrated).

As such, in the drug injection device according to the exemplary embodiment, the switch unit 180 is installed in the injection unit 110, and as a result, the operator can easily use the drug injection device without using a heavy type like the related art. Further, the operator can rapidly and easily perform the injection and the injection stop of the injectable solution J as compared with a pedal type in which the injection of the drug is controlled by a pedal.

Meanwhile, the drug injection device according to the exemplary embodiment further includes a chargeable battery (not illustrated) which is provided in the injection speed adjustment unit 120 and supplies power to the driving motor 152, a first coil (not illustrated) which is provided in the injection speed adjustment unit 120 and charges the chargeable battery, and a non-contact charging cradle 200 which is non-contacted to the first coil and provided with a second coil (not illustrated) supplying electric energy to the first coil.

The first coil (not illustrated) is embedded in the injection speed adjustment unit 120 and the second coil is embedded in the non-contact charging cradle 200. The first coil receives current from the second coil while not being connected to the second coil through an access terminal and the like. That is, a magnetic field generated in the second coil is induced in the first coil to supply the current to the first coil.

As such, in the drug injection device according to the exemplary embodiment, the chargeable battery is charged by a non-contact point method to be easily charged and a contact point defect is not generated to prevent a damage caused by short circuit and the like.

An operation of the drug injection device having the configuration will be described.

First, the operator manipulates the controller portion (not illustrated) after determining the injection speed of the injectable solution J so that the person being operated on does not feel pain when injecting the injectable solution J into the person being operated on to set the pressurizing speed of the pressurizing plunger 140.

Next, in order to inject the injectable solution J, the intra-injection needle 114 is inserted to the operating site.

Thereafter, the operator manipulates the button 181 of the switch unit 180 to control the pressure applied to the injectable solution J.

When the operator manipulates the switch unit 180 to indicate the injection to the control unit, the pressurizing plunger 140 applies the pressure to the piston M3 and the injectable solution J in the ampoule M is injected into the body of the person being operated on by movement of the piston M3.

In the process of injecting the injectable solution J, the operator presses the button 181 of the switch unit 180 to stop the injection of the injectable solution J according to a state change of the person being operated on.

As such, in the drug injection device according to the exemplary embodiment, the pressurizing plunger 140 of the injection speed adjustment unit 120 pressurizes the injectable solution J and thus, it is not necessary for the person being operated on to directly pressurize the injectable solution J for the injection of the injectable solution J. The pressurizing plunger up/down driving module 150 which drives the pressurizing plunger 140 up and down is provided on the same axis as the pressurizing plunger 140 to reduce the injection speed adjustment unit 120 in size and thickness.

Although the exemplary embodiments have been described in detail with reference to the drawings, the scopes of the exemplary embodiments are limited to the aforementioned drawings and description.

The present invention is not limited to the embodiments described herein, and it would be apparent to those skilled in the art that various changes and modifications might be made without departing from the spirit and the scope of the present invention. Accordingly, it will be determined that the changed examples or modified examples are included in the appended claims of the present invention.

INDUSTRIAL APPLICABILITY

The present invention relates to a drug injection device and can be used in medical industry, particularly, dental industry.

The invention claimed is:
1. A drug injection device, comprising:
an injection unit which is provided with an ampoule accommodation portion for accommodating an ampoule that contains an injectable solution, and is configured to inject the injectable solution into a person being operated on;
an injection speed adjustment unit which is connected to the injection unit, applies pressure to the injectable solution, and adjusts an injection speed of the injectable solution, being injected into the person being operated on, by selectively adjusting a speed of the pressure applied to the injectable solution;
a chargeable battery which is provided in the injection speed adjustment unit and supplies power to a driving motor;

a first coil which is provided in the injection speed adjustment unit and charges the chargeable battery; and
a non-contact charging cradle which is non-contacted to the first coil and provided with a second coil supplying electric energy to the first coil,
wherein the injection speed adjustment unit comprises:
a housing;
an injection unit attachment portion to which the ampoule accommodation portion is detachably attached;
a pressurizing plunger which is connected to the ampoule accommodated in the ampoule accommodation portion and applies pressure to the injectable solution;
a pressurizing plunger up/down driving module which is provided on the same axis as the pressurizing plunger and drives the pressurizing plunger up or down; and
a waterproof portion through which the pressurizing plunger passes and that prevents a liquid from penetrating to the inside of the injection speed adjustment unit,
wherein the injection unit attachment portion comprises:
a body portion for injection unit attachment provided in an insertion groove to which an end region of the ampoule accommodation portion is inserted; and
a locking jaw portion provided at the body portion for injection unit attachment and locked to a projection member projecting in a lateral direction from an outer wall of the ampoule accommodation portion when the ampoule accommodation portion rotates,
wherein the locking jaw portion comprises:
an upper locking jaw supporting an upper end of the projection member; and
a lower locking jaw supporting a lower end of the projection member and elastically biasing the lower end of the projection member toward the upper locking jaw,
wherein the pressurizing plunger up/down driving module comprises:
a lead screw engaging with the pressurizing plunger;
the driving motor, wherein the driving motor is adapted to rotate the lead screw; and
a guide portion that guides movement of the pressurizing plunger, wherein the guide portion includes an exposure hole through which the pressurizing plunger is exposable when driven up or down; and
a detection sensor adjacent to the exposure hole and configured to detect whether the pressurizing plunger is exposed by the exposure hole,
wherein the housing accommodates the injection unit attachment portion, the pressurizing plunger, the pressurizing plunger up/down driving module and the waterproof portion, and wherein the pressurizing plunger is accommodated inside a main body of the injection unit attachment portion and the guide portion of the pressurizing plunger up/down driving module, and the waterproof portion is accommodated inside the main body,
wherein the pressurizing plunger comprises a plunger main body and a plunger cap being attached to an upper end of the plunger main body, the plunger cap comprises:
a cap body portion connected to the plunger main body and having a cylindrical shape;
a neck portion connected to the cap body portion;
a cap head portion connected to the neck portion; and
an airtight member supported by the neck portion.

2. The drug injection device of claim 1,
wherein the guide portion comprises a rotation stop portion which stops rotation of the pressurizing plunger.

3. The drug injection device of claim 2,
wherein the rotation stop portion comprises a non-curved inner wall portion shape-matched with a non-curved side portion formed on an outer wall of the pressurizing plunger.

4. The drug injection device of claim 1,
wherein the locking jaw portion further includes a stopper that supports a front end of the projection member and limits rotation of the ampoule accommodation portion.

5. The drug injection device of claim 1,
wherein the waterproof portion comprises:
a waterproof portion body with a through-hole through which the pressurizing plunger passes; and
a watertight member supported by the waterproof portion body and sealing a gap between an outer wall of the pressurizing plunger and a side wall of the through-hole.

6. The drug injection device of claim 1,
wherein the injection speed adjustment unit further comprises:
a control unit that controls the pressurizing plunger up/down driving module to vary a pressurizing speed of the pressurizing plunger; and
a controller portion electrically connected with the control unit.

7. The drug injection device of claim 6, further comprising:
a switch unit which is attached to the injection unit and connected to the control unit wiredly or wirelessly to transmit a signal to the control unit.

8. The drug injection device of claim 7,
wherein the switch unit comprises:
a panel portion with a button which turns on/off the pressurization of the injectable solution; and
a panel bracket which is attached to the injection unit and supports the panel portion.

9. The drug injection device of claim 1,
wherein the injection unit further comprises:
a tube connected to the ampoule accommodation portion;
a needle holder connected to the tube; and
an intra-injection needle attached to the needle holder.

10. The drug injection device of claim 9,
wherein the ampoule accommodation portion comprises:
an accommodation portion main body accommodated with the ampoule; and
an ampoule needle attached to the accommodation portion main body and communicating with the tube.

11. The drug injection device of claim 9,
wherein the injection speed adjustment unit further comprises a needle holder bracket gripping the needle holder.

* * * * *